United States Patent
Niemeyer et al.

(10) Patent No.: US 6,187,941 B1
(45) Date of Patent: *Feb. 13, 2001

(54) PROCESS FOR THE PREPARATION OF OXAZAPHOSPHORINE-2-AMINES

(75) Inventors: Ulf Niemeyer, Bielefeld; Harald Niegel, Coswig; Bernard Kutscher, Maintal; Ion Neda, Braunschweig, all of (DE)

(73) Assignee: Asta Medica Aktiengesellschaft, Dresden (DE)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/149,099

(22) Filed: Sep. 8, 1998

(30) Foreign Application Priority Data

Sep. 6, 1997 (DE) .............................. 197 39 159

(51) Int. Cl.$^7$ ...................................... C07F 9/24
(52) U.S. Cl. ............................................. 558/81
(58) Field of Search .............. 558/81; 514/110; 548/956

(56) References Cited

U.S. PATENT DOCUMENTS

| 3,732,340 | * | 5/1973 | Arnold | ..... | 558/81 |
| 4,238,423 | * | 12/1980 | Sato | ..... | 558/81 |
| 4,239,709 | * | 12/1980 | Sato | ..... | 558/81 |

FOREIGN PATENT DOCUMENTS

| 1057119 | * | 2/1956 | (DE) . |
| 1235022 | * | 6/1971 | (GB) . |

OTHER PUBLICATIONS

CA:89:109387 by Kinas abs in Bull. Acad Pol. Sci. Ser. Sci. Chim 26 (1) pp. 39–42, 1978.*
CA:114:102388 by Stec abs of PL149593 Feb. 1990.*
CA:83:96406 by Kajita abs of JP50062912 May 1975.*
CA:112:228511 by Semmoud abs of J Fluorine Chem 46 (1) pp. 1–6, 1990.*
CA:110:75332 by Pavel abs of DD257257 Jun. 1988.*
CA:114:101109 by Masini abs of EP383675 Aug. 1990.*
CA:70:11021 by Hillers abs of Puti Sin. Izyskaniya Protivoopukholevykh Prep Tr. Simp 2nd Moscow Meeting date 1965 pp. 81–4, 1967.*

Sato, Oxazaphospholine derivatives, Chemical Abstracts, vol. 093, No. 3, Jul. 21, 1980, Abstract No. 026467c.
Preparation of ifosfamide, Chemical Abstracts, vol. 107, No. 1, Jul. 6, 1987, Abstract No. 007385r.
1,3,2–Oxaazaphosphorinane–2–oxide derivatives, Chemical Abstracts, vol. 101, No. 11, Sep. 10 1984, Abstract No. 091231u.
Stec, W.J. et al., Optically active derivatives of 1,3,2–oxazaphosphorinane, Chemical Abstracts, vol. 100, No. 5, Jan. 30 1984, Abstract No. 034702d.
Stec, W.J. et al., Preparation of 2H–N–acyltetrahydro–2–oxo–1,3,2–oxazaphosphorines, Chemical Abstracts, vol. 114, No. 11, Mar. 18 1991, Abstract No. 102388x.

* cited by examiner

*Primary Examiner*—Jean F Vollano
(74) *Attorney, Agent, or Firm*—Pillsbury Madison & Sutro LLP

(57) ABSTRACT

A process for the preparation of oxazaphosphorine-2-amines of the formula (I) described by the reaction scheme

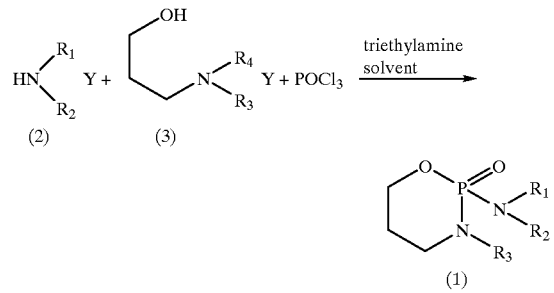

in which $R_1$ is H, 2-bromoethyl, 2-chloroethyl, 2-hydroxyethyl, 2-mesyloxyethyl or 1-phenylethyl; $R_2$ is H or 2-chloroethyl; $R_3$ is H, 2-bromoethyl, 2-chloroethyl or 1-phenylethyl; and $R_4$ is H; or $R_1$ and $R_2$, and also $R_3$ and $R_4$, together with the linked N atom, form an aziridide ring, where $R_1$, $R_2$ and $R_3$ are not simultaneously H, and $R_1$ and $R_3$ are not simultaneously 1-phenylethyl; and Y, which is optionally present, is hydrogen chloride or hydrogen bromide. The reaction is carried out in a single vessel with phosphoryl chloride and an auxiliary base as an acid-binding agent with minimization of the effect of water and without isolation of an intermediate compound.

11 Claims, No Drawings

PROCESS FOR THE PREPARATION OF OXAZAPHOSPHORINE-2-AMINES

BACKGROUND OF THE INVENTION

1. Field of the Invention

The invention relates to a process for the preparation of racemic and diastereomeric oxazaphosphorine-2-amines (N-substituted tetrahydro-2H-$\sigma^4\lambda^5$-1,3,2-oxazaphosphorine-2-amino-2-oxides [sic]) of the general formula 1

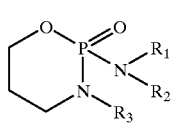

(1)

in which $R_1$ can be H, 2-bromoethyl, 2-chloroethyl, 2-hydroxyethyl, 2-mesyloxyethyl and 1-phenylethyl, $R_2$ can be H and 2-chloroethyl and $R_3$ can be H, 2-bromoethyl, 2-chloroethyl and 1-phenylethyl, or $R_1$ and $R_2$, together with the linked N atom, form an aziridine ring. The compounds prepared by the novel process are either cytostatics or immunosuppressants themselves or starting compounds for the preparation of racemic and enantiomerically pure oxazaphosphorine-2-amines having cytostatic or immunosuppressant activity.

2. Background Information

The compounds of the formula 1 include the known medicaments cyclophosphamide ($R_1=R_2=$2-chloroethyl, $R_3=$H), ifosfamide ($R_1=R_3=$2-chloroethyl, $R_2=$H) and trofosfamide ($R_1=R_2=R_3=$2-chloroethyl). They have been used in cancer therapy since 1958 or the 1970s (N. Brock, Cancer Res. 49, 1–7 (1989)). Their synthesis is described in the Patent Specifications DE 1 057 119, GB 1 235 022 and DE 1 645 921. The compounds according to formula 1 furthermore include sufosfamide ($R_1=$2-mesyloxyethyl, $R_2=$H, $R_3=$2-chloroethyl), which was developed as an immunosuppressant for autoimmune diseases (DE 2 107 936, DE-A 2 201 675), as well as compounds which are suitable for the preparation of the mentioned oxazaphosphorine-2-amines in their racemic or enantiomeric form (K. Pankiewicz et al., J. Amer. Chem. Soc. 101, 7712–7718 (1979) and K. Misiura et al. J. Med. Chem. 26, 674–679 (1983)).

It is common to the syntheses known from the literature that, as a phosphorus-containing starting compound, 2-chlorotetrahydro-2H-1,3,2-oxazaphosphorine-2-oxide, bis(2-chloroethyl)dichlorophosphoramide or 2-chloro-3-(2-chloroethyl)tetrahydro-2H-1,3,2-oxazaphosphorine-2-amino-2-oxide [sic] is reacted in one synthesis step to give oxazaphosphorine-2-amine. The three phosphorus-containing starting compounds are prepared, for their part, from phosphoryl chloride (R. H. Iwamato et al. J. Org. Chem. 26, 4743–4745 (1961), O. M. Friedman et al., J. Amer. Chem. Soc. 76, 655–658 (1954) and J. M. S. van Maanen et al., J. Labelled Compd. Radiopharm. 18, 385–390 (1981)).

These syntheses have disadvantages. The total yield of the oxazaphosphorine-2-amines, based on phosphoryl chloride, remains significantly below 50% and is therefore relatively low for a two-stage synthesis. Furthermore, the isolation of the intermediate, i.e. one of the three abovementioned phosphorus-containing starting compounds, is unfavorable, since they are thermally and hydrolytically unstable and can give rise to side reactions during preparation, storage or shortly before use. Additionally, the advantages of a two-stage one-pot reaction are not utilized.

SUMMARY OF THE INVENTION

The object was therefore to achieve a process which, compared with the known prior art, has the following advantages:

1. higher total yield,
2. avoidance of the isolation of intermediates,
3. lower outlay in terms of apparatus,
4. decreased time requirement,
5. lower substance requirement,
6. avoidance of chromatographic or other additional purification steps and
7. reduced cytostatic and chemical waste and thus lower environmental pollution.

The solution of the problem according to the invention consists in reacting a phosphoryl halide and two amines in an inert organic solvent and using an auxiliary base, with minimization of the effect of water and of alcohols and also without isolation of an intermediate compound, to give the compounds of the general formula I. As a rule, the process is carried out as a two-stage one-pot reaction in which the reaction participants are added successively to the reaction vessel.

For the successful implementation of the novel process, it is crucial that the effect of water, in particular on phosphoryl chloride, is suppressed. On the basis of the extensive investigation of the inventors, it was demonstrated that with increasing water content in the reaction mixture the number and amount of by-products increases and the yield of the target compounds is drastically reduced. The crystallization of the final products is then no longer possible or only possible after additional purification steps, e.g. chromatography. This surprising effect of water on the success of the synthesis was still not taken into account in the literature until now. Instead of this, the difficulties of a two-stage one-pot synthesis which starts from phosphoryl chloride were avoided. The only obviously advantageous one-stage synthesis was selected, in which one of the three abovementioned phosphorus-containing starting compounds was used.

In addition to water, attention is to be paid to the absence of alcohols. Thus it was possible to show that traces of methanol and ethyl alcohol in the solvents can lead to side reactions and yield reduction.

The phosphoryl halides have the general formula 2 and the two amines the general formulae 3 and 4:

(2)

(3)

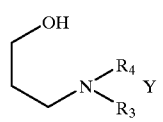

(4)

in which $R_1$, $R_2$ and $R_3$ have the same meaning as in formula 1, $R_4$ can be H, or $R_3$ and $R_4$, together with the linked N atom, form an aziridine ring, X is chlorine or bromine, X only being bromine if $R_1$ or $R_3$ is 2-bromoethyl, and Y has no meaning or can be hydrogen chloride or hydrogen bromide. The optically active amine used for the preparation of two diastereomeric compounds of the formula 1 is thus (R)-(+)- or (S)-(−)-1-phenylethylamine or an N-3-hydroxypropyl derivative of (+)-or (−)-1-phenylethylamine.

The reaction is carried out in inert organic solvents or solvent mixtures, dichloromethane, 1,2-dichloroethane, chloroform, dioxane, acetonitrile, tetrahydrofuran and toluene, for example, being suitable.

A suitable auxiliary base or acid-binding agent is, for example, triethylamine, pyridine and sodium carbonate.

The concentration of the reaction mixture, i.e. the ratio of compound of the formula 2, 3 or 4 to the volume of the solvent, can vary between 0.1 to [sic] 6 mol per liter.

The amines of the general formulae 3 and 4 are employed, as a rule, in equimolar amount based on the compound of the formula 2, a stoichiometric deficit of up to 5% or a 20% excess being possible.

The auxiliary base is employed, as a rule, in an equivalent amount to the amine, i.e. for the condensation of the compound of the formula 3, two equivalents of auxiliary base are needed if it is present as a salt, and one equivalent of auxiliary base if it is present as a free base. For the compounds of the formula 4, correspondingly, three or two equivalents respectively are used. An up to 30 percent excess of auxiliary base is possible.

The condensation reaction of the phosphoryl halide with the amines proceeds exothermically. To control the reaction temperature, the reaction component with which the condensation is set off is slowly added with cooling. Therefore phosphoryl chloride, for example, is slowly added dropwise to an amine which is present as the free base, or the auxiliary base is slowly added to a mixture of phosphoryl chloride and an amine which is present as a salt. In the initial phase, the reaction temperature is kept, as a rule, in the temperature range from −40° C. to 20° C., in particular between −20 and +10° C., by cooling. It can increase after half of the reaction has taken place to 100° C. or up to the boiling temperature of the solvent—if appropriate by heating.

The compounds of the formulae 2 to 4 and the auxiliary base are added together at specific times. The following standard batch with its variations is intended to clarify this.

An amine of the formula 3 and the equivalent amount of auxiliary base are initially introduced in the solvent, and a compound of the formula 2 is slowly added dropwise or run in (first step). Subsequently, the compound of the formula 4 is added and then the auxiliary base is slowly metered in (second step).

This standard batch can be varied in the first step such that compound of the formula 2 is initially introduced and the amine of the formula 3 is then slowly added, together with the auxiliary base. Furthermore, the amine of the formula 3 can be initially introduced in the solvent in its salt form, compound of the formula 2 added and then the auxiliary base slowly metered in. In addition, auxiliary base and compound of the formula 2 can slowly be added separately to the initially introduced amine of the formula 3 at the same time, where the two additions should be mutually displaced such that the auxiliary base is present in an excess to the compound of the formula 2.

In the second step, the compound of the formula 4 can also be added slowly together with the auxiliary base; or the compound of the formula 4 and the auxiliary base is [sic] initially introduced and the reaction mixture from the first step is slowly added.

The standard batch can be varied such that the amine of the formula 4 is employed in the first step and the amine of the formula 3 in the second step. The total auxiliary base for both stages can also be employed in the first step. The simultaneous, slow addition of the two amines with the auxiliary base to the initially introduced phosphoryl chloride is also possible.

Other times than described here for the addition of the four components are also possible for the process. However, it is, for example, unfavorable to initially introduce phosphoryl chloride together with triethylamine or to initially introduce 2-chloroethylamine hydrochloride together with the auxiliary base and to add phosphoryl chloride.

If the reaction is carried out in two steps, after the first step, as a rule, the mixture is stirred for 30 minutes or longer (expediently often overnight). Phosphoryl chloride as a result reacts to give defined intermediate compounds known from the literature. Thus the compound 2-chlorotetrahydro-2H-1,3,2-oxazaphosphorine-2-amino-2-oxide [sic] is formed with 3-amino-1-propanol, the compound bis-N,N-(2-chloroethyl)dichlorophosphoramide with bis(2-chloroethyl)amine hydrochloride, the compound 2-chloro-3-(2-chloroethyl)tetrahydro-2H-1,3,2-oxazaphosphorine-2-amino-2-oxide [sic] with N-(2-chloroethyl)-3-hydroxypropylamine hydrochloride or 3-N-hydroxypropylaziridine and the compound N-(2-chloroethyl)dichlorophosphoramide with 2-chloroethylamine hydrochloride.

To decrease water in the reaction medium, all substances and equipment employed are used in a form which is as anhydrous as possible. Thus, for example, equipment is heated thoroughly to remove residual moisture, predried solvents are employed, the hygroscopic amines of the formulae 3 and 4 are dried briefly before use, the phosphoryl halides are freshly distilled under dry conditions and the auxiliary base is appropriately predried. Before the start of the reaction, the reaction solution should have a water content of below 0.5%, but better of below 0.1% or below 0.001%.

The formation of by-products can also be decreased if the reaction mixture is treated with additives before the start of the reaction. Such additives can be, for example, molecular sieve, alumina in its various forms, calcium chloride (anhydrous or a hydrate form), phosphorus pentoxide and magnesium chloride. As a rule, the addition is between 5 g and 150 g per mol of compound of the formula 2 employed and the solution or suspensions [sic] is stirred for one half to 3 hours before the condensation reaction is started by addition of the auxiliary base or of the phosphoryl halide. It is favorable here to work in a homogeneous phase. For example, 3.9 g of N-2-chloroethyl-3-hydroxypropylamine hydrochloride go completely into solution in 60 ml of dichloromethane after addition of 3.2 ml of triethylamine (see Example 3).

After the first or, alternatively, second chlorine atom of the phosphoryl halide has reacted, the possibility exists of separating off the precipitated salts or washing the reaction mixture and then completing the reaction by addition of amine and auxiliary base.

The working-up of the reaction mixture at the end of the reaction is carried out by filtering off the salts, and/or by washing with water at various pHs. The hydrolyzability and water solubility of the oxazaphosphorine-2-amines, e.g. by a short contact time with the acid or cooling of the batch, is to be considered here. The anhydrous working-up of the reaction mixture is also favorable or the neutralization of the reaction solution by HCl gas to pH 4 to 6. In addition, the use of weak acids, e.g. acetic acid and oxalic acid, is suitable.

In principle, the amines of the formulae 3 and 4 can also be employed in impure form. For example, N-(2-chloroethyl)-3-hydroxypropylamine hydrochloride can also be used in the presence of 15% N-(2-chloroethyl)-3-chloropropylamine hydrochloride for the synthesis of a compound of the formula 1 (see Example 2). A more than 10% side reaction was to be expected, such that the recovery of the compound of the formula 1 is made difficult or even prevented. Surprisingly, only a minimum loss of yield occurred. The purification of N-(2-chloroethyl)-3-hydroxypropylamine hydrochloride, which is very complicated, can therefore be omitted. This is a significant advantage in the synthesis.

The compounds according to the invention also include oxazaphosphorine-2-amines which are suitable for conversion to cyclophosphamide, ifosfamide, trofosfamide and sufosfamide. Thus the two diastereomers prepared in Example 5 can be separated in the manner described (K. Misiura et al.). The (1'R,2R) -isomer is then hydrogenated to give (R)-ifosfamide. In addition, the precursor of sufosfamide, i.e. N-(2-chloroethyl)-2-(2-hydroxyethyl) tetrahydro-2H-1,3,2-oxazaphosphorine-2-amino-2-oxide [sic], is accessible and can be directly further mesylated to give sufosfamide (see Example 8).

It was possible to considerably improve the yield of the compounds of the formula 1 according to the invention. This will be seen in the following with the aid of the comparison between the total yield based on phosphoryl chloride, which can be calculated from previously published yields (for references see above) for the two stages, and the yield for the Examples 3, 5, 6 and 8.

Thus the yield based on phosphoryl chloride for 2-chloro-3- (2-chloroethyl)tetrahydro-2H-1,3,2-oxazaphosphorine-2-amino-2-oxide [sic] is 49% (J. M. S. van Maanen, page 388). The yield based on 2-chloro-3-(2-chloroethyl)tetrahydro-2H-1,3,2-oxazaphosphorine-2-amino-2-oxide [sic] for ifosfamide is 71% (DE 1 645 921: Example 4, columns 6 and 7), so that a total yield of 35% of ifosfamide can be calculated. Consequently the yield according to the novel process (Example 3, yield 73%) is twice as high.

The yield based on phosphoryl chloride for bis(2-chloroethyl)dichlorophosphoramide is 16% (O. M. Friedman, p. 657). The yield based on bis(2-chloroethyl) dichlorophosphoramide for cyclophosphamide monohydrate is 65–70% (DE 1 057 119: Example 10, column 9), so that a total yield of 11% can be calculated. The yield according to the novel process (Example 6, 72% yield of cyclophosphamide monohydrate) is thus considerably higher.

The yield based on 2-chloro-3-(2-chloroethyl)tetrahydro-2H-1,3,2-oxazaphosphorine-2-amino-2-oxide [sic] for the compound of the general formula 1 in which $R_1$ is 1-phenylethyl, $R_2$ is H and $R_3$ is 2-chloroethyl is 68% (a 1:1 diastereomer mixture, K. Misiura, p. 677), so that a total yield of 34% results. The yield according to the novel process is thus almost twice as high at 66% (Example 5), so that (R)-ifosfamide is also accessible in almost twice the yield using the novel process.

Sufosfamide was previously prepared starting from 2-chloro-3-(2-chloroethyl)tetrahydro-2H-1,3,2-oxazaphosphorine-2-amino-2-oxide [sic] in a yield of 30% (DE 2 107 936: Example 9, columns 8 and 9), so that a total yield of 15% based on phosphoryl chloride can be calculated. According to the novel process, the yield of sufosfamide is 38% (Example 8) and is thus more than twice as high.

In addition to the yield improvements, the other abovementioned, desired advantages have also been achieved. Thus for sufosfamide chromatographic purification is no longer necessary. Ifosfamide can be prepared according to Example 1 in such a way that 2-chloroethylamine hydrochloride is employed in the 1st step and N-(2-chloroethyl)-3-hydroxypropylamine hydrochloride is employed in the 2nd step. This process was previously not possible. The isolation of the intermediate is avoided in all examples, as a result of which crucial simplifications and process improvements are achieved. The novel process is an enormously advantageous process for industrial synthesis in the economical and ecological respect.

DETAILED DESCRIPTION OF THE INVENTION

The following examples serve to illustrate the present invention further, without restricting it thereto.

EXAMPLE 1

N,3-Bis(2-chloroethyl)tetrahydro-2H-1,3,2-oxazaphosphorine-2-amino-2-oxide [sic] (ifosfamide)

4.18 g of 2-chloroethylamine hydrochloride are suspended in a solution of 5.52 g of phosphoryl chloride in 80 ml of dichloromethane cooled to about 0° C. and 10 ml of triethylamine are added dropwise with stirring at 0–10° C. in the course of 1 hour. 6.3 g of N-(2-chloroethyl)-3-hydroxypropylamine hydrochloride are then added to the reaction mixture and 15 ml of triethylamine are added dropwise with stirring. After stirring at room temperature for 6 hours, the mixture is extracted by shaking with twice with 10 ml of dilute hydrochloric acid (wash water with >pH 2), with 10 ml dilute sodium carbonate solution and twice with 10 ml of water. The organic phase is dried over sodium sulfate and concentrated in vacuo. It is then taken up in 100 ml of diethyl ether, and the solution is filtered through carbon and concentrated. The residue is dissolved in 30 ml of diethyl ether and is stored at −5° C. for crystallization. On the next day, the solid is filtered off with suction and dried.

Yield 5.3 g (56% of theory), melting point: 48–51° C. Thin-layer chromatography using prepared TLC plates, silica gel $60_{F245}$ from Merck. This TLC method was also used in the following examples. $R_F$ value=0.58 ($CH_2Cl_2:CH_3OH=90:10$), $R_F$ value=0.30 ($CH_2Cl_2:CH_3OH=95:5$)

$^1$H-NMR(500 MHz, CDCl$_3$): δ=1.9–2.0 (m, 2H, CH$_2$), 3.2–3.5 (m, 7H, 3 CH$_2$, NH), 3.6 (t, 2H, CH$_2$—Cl), 3.6–3.7 (m, 2H, CH$_2$—Cl), 4.2–4.4 (m, 2H, CH$_2$—O)

$^{31}$P-NMR (202 MHz, CDCl$_3$): δ=12.6

EXAMPLE 2

N,3-Bis(2-chloroethyl)tetrahydro-2H-1,3,2-oxazaphosphorine-2-amino-2-oxide [sic] (ifosfamide)

20.4 g of N-(2-chloroethyl)-3-hydroxypropylamine hydrochloride (85% strength) and 42 ml of triethylamine are added to 300 ml of dichloromethane with stirring at 0°C.–10° C. 15.3 g of phosphoryl chloride are then added dropwise with stirring. After one hour at room temperature, 12.8 g of 2-chloroethylamine hydrochloride and 30.8 ml of triethylamine are added with cooling at 15° C. and the mixture is stirred overnight at room temperature. Working-up is carried out as in Example 1. The crystallization is carried out in tert-butyl methyl ether.

Yield: 17 g (65% of theory), melting point: 47–50° C. $R_F$ values and NMR data correspond to those of Example 1.

EXAMPLE 3

N,3-Bis(2-chloroethyl)tetrahydro-2H-1,3,2-
oxazaphosphorine-2-amino-2-oxide [sic]
(ifosfamide)

3.87 g of N-(2-chloroethyl)-3-hydroxypropylamine hydrochloride (90% strength), 0.2 g of calcium chloride and 3.2 ml of triethylamine are stirred at 0° C. for 60 min in 60 ml of dichloromethane which contains about 0.1% of water. Simultaneously and at a maximum of 5° C., 6.0 ml of triethylamine are then added dropwise at a drop rate of 1 ml/min and 3.07 g of phosphoryl chloride at a drop rate of 0.3 ml/min. The mixture is then stirred at 0° C. for a further 2 hours and treated with 2.5 g of 2-chloroethylamine hydrochloride. After addition of 5.6 ml of triethylamine, it is stirred at room temperature for a further 10 hours, the reaction solution is brought to pH 4–6 by introduction of HCl gas, and extracted by shaking once with 12 ml of water and twice with 2.5 ml of sodium carbonate solution. Further working-up as in Example 1.

Yield: 3.9 g (73% of theory), melting point: 49–51° C. $R_F$ values and NMR data correspond to those of Example 1.

EXAMPLE 4

N,3-Bis(2-chloroethyl)tetrahydro-2H-1,3,2-
oxazaphosphorine-2-amino-2-oxide [sic]
(ifosfamide)

15.3 g of phosphoryl chloride are added to 200 ml of dichloromethane with stirring at 0° C. and treated with stirring at 0 to 20° C. with a solution of 10 g of N-3-hydroxypropylaziridine in 14.6 ml of triethylamine. On the next day, 12 g of 2-chloroethylamine hydrochloride are added and then 29 ml of triethylamine are added dropwise. Working-up is carried out as in Example 1.

Yield: 18 g (69% of theory), melting point: 47–50° C. $R_F$ values and NMR data correspond to those of Example 1.

EXAMPLE 5

(1'R,2R) and 1'R,2S)-3-(2-chloroethyl)-2-(1'-
methylbenzyl)tetrahydro-2H-1,3,2-
oxazaphosphorine-2-amino-2-oxide [sic] (The (1'R, 2R) isomer is the starting material for the synthesis of (R)-ifosfamide.)

17.4 g of N-(2-chloroethyl)-3-hydroxypropylamine hydrochloride and 42 ml of triethylamine are added to 300 ml of dichloromethane with stirring at 0° C. 15.3 g of phosphoryl chloride are then added dropwise with stirring. After one hour at room temperature, a mixture of 12.6 g of (R)-(+)-1-phenylethylamine ($[\alpha_D^{23}]$=+38°, neat) and 14.7 ml of triethylamine is added with cooling at 5 to 10° C. On the next day, the reaction solution was worked up as in Example 1 and the residue was crystallized in diethyl ether.

Yield: 20 g (66% of theory) $R_F$ value=0.22 and 0.18 (hexane:chloroform:tert-butyl alcohol=4:2:1), $R_F$ value= 0.66 ($CH_2Cl_2:CH_3OH$=90:10), $R_F$ value=0.23 ($CH_2Cl_2:CH_3OH$=95:5) $[\alpha_D^{25}]$=+39° (c=3, $CH_3OH$)

$^1$H-NMR(500 MHz, $CDCl_3$): δ=1.5 (d, 6H, 2 $CH_3$), 1.8–2.0 (m, 4H, 2 $CH_2$—O), 2.9–3.5 (m, 14H, 12 $CH_2$, 2 CH), 3.6 (m, 2H, $CH_2$—Cl), 4.0–4.4 (m, 4H, 2 $CH_2$—O), 7.2–7.4 (m, 10H, phenyl-H)

In the $^{31}$P-NMR spectrum (202 MHz, $CDCl_3$), the 1:1 diastereomer mixture is confirmed by two signals of equal intensity at δ=11.2 and 10.9 ppm.

EXAMPLE 6

N,N-Bis(2-chloroethyl)tetrahydro-2H-1,3,2-
oxazaphosphorine-2-amino-2-oxide [sic],
monohydrate (cyclophosphamide monohydrate)

15.3 g of phosphoryl chloride are added to a suspension of 17.8 g of N,N-bis(2-chloroethyl)amine hydrochloride in 200 ml of dichloromethane and then 29 ml of triethylamine are added dropwise at 0 to 10° C. After 3 hours, a mixture of 7.6 ml of 3-amino-1-propanol and 28 ml of triethylamine is added at a maximum of 15° C. On the next day, the mixture is washed with 80 ml of ice water, the aqueous phase is extracted with dichloromethane, the combined dichloromethane phases are concentrated, the residue is taken up with diethyl ether, and the solution is treated with active carbon, filtered and saturated with water. After crystallization at 0° C., the solid was filtered off with suction and dried.

Yield: 20 g (72% of theory), melting point 50–52° C. $R_F$ value=0.58 ($CH_2Cl_2:CH_3OH$=90:10), $R_F$ value=0.24 ($CH_2Cl_2:CH_3OH$=95:5)

$^1$H-NMR(500 MHz, $CDCl_3$): δ=1.8–2.0 (m, 2H, $CH_2$), 2.6 ($H_2O$), 3.2–3.6 (m, 7H, 3 $CH_2$—N, NH), 3.6–3.7 (t, 4H, $CH_2$—Cl), 4.2–4.3 (m, 1H, $CH_2$—O), 4.3–4.5 (m, 1H, $CH_2$—O)

$^{31}$P-NMR (202 MHz, $CDCl_3$): δ=13.0

EXAMPLE 7

N,N-Bis(2-chloroethyl)tetrahydro-2H-1,3,2-
oxazaphosphorine-2-amino-2-oxide [sic],
monohydrate (cyclophosphamide monohydrate)

15.3 g of phosphoryl chloride are added with stirring at 2 to 15° C. to a solution of 7.6 g of 3-amino-1-propanol and 28 ml of triethylamine in 200 ml of dichoromethane. After 1 day at room temperature, 29 ml of triethylamine is added dropwise to 17.8 g of N,N-bis(2-chloroethyl)amine hydrochloride at 10 to 20° C. [sic]. The solution is then heated under reflux for several hours. Working-up is carried out as in Example 4 and the residue is recrystallized from ethanol/water (3:5).

Yield: 19 g (68% of theory), melting point 49–52° C. $R_F$ values and NMR data correspond to those of Example 6.

EXAMPLE 8

N-(2-Chloroethyl)-2-(2-mesyloxyethyl)tetrahydro-
2H-1,3,2-oxazaphosphorine-2-amino-2-oxide [sic]
(sufosfamide)

26.1 g of N-(2-chloroethyl)-3-hydroxypropylamine hydrochloride and 23.0 g of phosphoryl chloride are suspended in 200 ml of dichloromethane and treated with 64 ml of triethylamine with vigorous stirring at 0 to 50° C. The mixture is then stirred at room temperature for 2 hours, the precipitate is filtered off and washed with dichloromethane, the combined organic phases are washed with ice water and dried over sodium sulfate, treated with active carbon and filtered. A solution of 8.8 g of ethanolamine in 21 ml of triethylamine is added with stirring at 15 to 20° C. and the mixture is stirred at room temperature for 3 hours. 20 ml of triethylamine are then added and 16.6 g of methanesulfonyl chloride are added dropwise at room temperature. The salts are filtered off and washed with dichloromethane. The combined organic phases are washed 4 times with saturated sodium chloride solution and the combined aqueous phases are extracted with dichloromethane. The combined organic phases are then dried with sodium sulfate, treated with active carbon and concentrated. The residue is taken up in a little dichloromethane, treated with diethyl ether and placed in the refrigerator for crystallization.

Yield: 18 g (38% of theory), melting point 77–79° C. $R_F$ value=0.60 ($CH_2Cl_2:CH_3OH=90:10$), $R_F$ value=0.18 ($CH_2Cl_2:CH_3OH=95:5$)

$^1$H-NMR(500 MHz, $CDCl_3$): δ=1.9 (m, 2H, $CH_2$), 3.1 (s, 3H, $CH_3$), 3.2–3.4 (m, 5H, $CH_2$—N), 3.4–3.5 (m, 1H, $CH_2$—N), 3.7 (t, 2H, $CH_2$—Cl), 3.7–3.8 (m, 1H, NH), 4.2–4.3 (m, 3H, $CH_2$—OP, $CH_2$—OS), 4.3–4.2 (m, 1H, $CH_2$—OP $^{31}$P-NMR (202 MHz, $CDCl_3$): δ=12.4

N-(2-Chloroethyl)-2-(2-hydroxyethyl)tetrahydro-2H-1,3,2-oxazaphosphorine-2-amino-2-oxide [sic] (Precursor for the mesylation of sufosfamide)

$R_F$ value=0.45 ($CH_2Cl_2:CH_3OH=90:10$)

$^1$H-NMR(500 MHz, $CDCl_3$): δ=1.9–2.0 (m, 2H, $CH_2$), 3.0–3.1 (m, 2H, $CH_2$—N), 3.2–3.3 (m, 3H, $CH_2$—N), 3.4–3.5 (m, 1H, $CH_2$—N), 3.6–3.7 (t, 2H, $CH_2$—N), 3.6–3.7 (m, 4H, $CH_2$—Cl, $CH_2O$), 4.0–4.1 (m, 1H, NH), 4.2–4.3 (m, 1H, $CH_2$—OP), 4.3–4.4 (m, 1H, $CH_2$—O), 4.1–4.8 (1H, OH)

$^1$H-NMR(500 MHz, DMSO-$D_6$): δ=1.7–1.8 (m, 1H, $CH_2$), 1.8–1.9 (m, 1H, $CH_2$), 2.7–2.8 (m, 2H, $CH_2$—N), 3.1–3.3 (m, 4H, $CH_2$—N), 3.4–3.5 (m, 1H, $CH_2$—O), 3.6–3.7 (t, 2H, $CH_2$—Cl), 4.1–4.2 (m, 2H, $CH_2$—OP), 4.5–4.6 (m, 2H, $CH_2$—O), 4.5–4.8 (1H, OH)

$^{31}$P-NMR (202 MHz, CDCl,): δ=14.2

EXAMPLE 9

N-(2-Chloroethyl)-2-(2-mesyloxyethyl)tetrahydro2H-1,3,2-oxazaphosphorine-2-amino-2-oxide [sic] (sufosfamide)

26.1 g of N-(2-chloroethyl)-3-hydroxypropylamine hydrochloride and 23.0 g of phosphoryl chloride are suspended in 200 ml of dichloromethane and treated with 64 ml of triethylamine with vigorous stirring at 0 to 5° C. The mixture is then stirred at room temperature for 2 hours. A solution of 8.8 g of ethanolamine in 21 ml of triethylamine is added with stirring at 15 to 20° C. and the mixture is stirred at room temperature for 3 hours. Mesylation and working-up is [sic] carried out analogously to Example 8.

Yield: 17 g (36% of theory), melting point 77–79° C. $R_F$ values and NMR data correspond to those of Example 8.

EXAMPLE 10

N,N-Bis(2-chloroethyl)-3-(2-chloroethyl)tetrahydro-2H-1,3,2-oxazaphosphorine-2-amino-2-oxide [sic] (trofosfamide)

15.3 g of phosphoryl chloride are added to a suspension of 17.8 g of N,N-bis(2-chloroethyl)amine hydrochloride in 200 ml of dichloromethane and then 28 ml of triethylamine are added dropwise at 0 to 10° C. After 3 hours, 17.4 g of N-(2-chloroethyl)-3-hydroxypropylamine hydrochloride and 42 ml of triethylamine are added with stirring at a maximum of 25° C. The reaction mixture is heated to reflux for 10 hours. On the next day, it is washed analogously to Example 1. The oily residue is taken up in diethyl ether, the solution is treated with active carbon, concentrated, and the residue is taken up in a little diethyl ether and the solution is crystallized at −10 to 0° C.

Yield: 17 g (54% of theory), melting point 50–52° C. $R_F$ value=0.85 ($CH_2Cl_2:CH_3OH=90:10$), $R_F$ value=0.42 ($CH_2Cl_2:CH_3OH=95:5$)

$^1$H-NMR(500 MHz, $CDCl_3$): δ=1.8–1.9 (m, 1H, $CH_2$), 2.0–2.1 (m, 1H, $CH_2$), 3.2–3.4 (m, 6H, 3 $CH_2$—N), 3.4–3.6 (m, 2H, $CH_2$—N), 3.6–3.8 (m, 6H, 3 $CH_2$—Cl), 4.2–4.3 (m, 1H, $CH_2$—O), 4.3–4.4 (m, 1H, $CH_2$—O)

$^{31}$P-NMR (202 MHz, $CDCl_3$): δ=13.8

EXAMPLE 11

N,N-Bis(2-chloroethyl)-3-(2-chloroethyl)tetrahydro-2H-1,3,2-oxazaphosphorine-2-amino-2-oxide [sic] (trofosfamide)

15.3 g of phosphoryl chloride are added to a suspension of 17.4 g of N-(2-chloroethyl)-3-hydroxypropylamine hydrochloride in 400 ml of dichloromethane and 46 ml of triethylamine are then added dropwise at 5 to 20° C. After 3 hours, 17.8 g of N,N-bis(2-chloroethyl)amine hydrochloride and 29 ml of triethylamine are added with stirring. The reaction mixture is heated to reflux for several hours. It is then cooled to room temperature, the dichloromethane phase is washed several times with water and the dried organic phase is concentrated. The oily residue is crystallized as in Example 10.

Yield: 21 g (64% of theory), melting point 50–52° C. $R_F$ values and NMR data correspond to those of Example 10.

What is claimed is:

1. A process for the preparation of oxazaphosphorine-2-amines of formula 1:

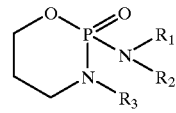

in which
R$_1$ is H, 2-bromoethyl, 2-chloroethyl, or 2-mesyloxyethyl;
R$_2$ is H or 2-chloroethyl; and
R$_3$ is H, 2-bromoethyl, 2-chloroethyl or 1-phenylethyl; or
R$_1$ and R$_2$, together with the linked N atom, form an aziridine ring;
said process comprising reacting a phosphoryl halide of formula 2, an amine of formula 3, and an amine of formula 4:

POX$_3$ (2)

(3)

HN(R$_1$)(R$_2$)—Y (4)

HO—CH$_2$CH$_2$CH$_2$—N(R$_4$)(R$_3$)—Y in which R$_1$, R$_2$ and R$_3$ have the same meanings as formula 1, R$_4$ is H, or R$_3$ and R$_4$, together with the linked N atom, form an aziridine ring, X is chlorine or bromine, X only being bromine if R$_1$ or R$_3$ is 2-bromoethyl, and Y, which is optionally present, is hydrogen chloride or hydrogen bromide; with an auxiliary base as an acid binding agent in the presence of inert solvents without isolation of an intermediate compound;

whereby, in a first step, one compound each of the formulae 2 and 3 are reacted and, in a second step, a compound of the formula 4 is reacted; or whereby, in a first step, one compound each of the formulae 2 and 4 are reacted and, in a second step, a compound of the formula 3 is reacted.

2. The process according to claim 1, wherein the auxiliary base is selected from the group consisting of pyridine, triethylamine, alkali metals and alkaline earth metal carbonates.

3. The process according to claim 1, wherein at least one halogenated, nonhalogenated, aromatic or aliphatic hydrocarbon is employed as a solvent.

4. The process according to claim 1, wherein toluene, chloroform, dichloromethane, dimethyl ether, tert-butyl methyl ether, dioxane or tetrahydrofuran is employed as solvent.

5. The process according to claim 1, wherein the compound N-(2-chloroethyl)-3-hydroxypropylamine hydrochloride which contains N-(2-chloroethyl)-3-chloropropylamine hydrochloride is used as a starting compound.

6. The process according to claim 1, wherein before the reaction is initiated the water content of the solution is below 0.5 percent.

7. The process according to claim 6, wherein before the reaction is initiated the water content of the solution is below 0.1 percent.

8. The process according to claim 7, wherein before the reaction is initiated the water content of the solution is below 0.001 percent.

9. The process according to claim 6, wherein the organic solvent has a water content of below 0.2 percent.

10. The process according to claim 9, wherein the organic solvent has a water content of below 0.05 percent.

11. The process according to claim 1 wherein X is chlorine and $R_1$, $R_2$ and $R_3$ independently represent H or 2-chloroethyl.

* * * * *